US006951959B2

(12) United States Patent
Ward et al.

(10) Patent No.: US 6,951,959 B2
(45) Date of Patent: *Oct. 4, 2005

(54) LOW PRESSURE PROCESS FOR MANUFACTURE OF 3-DIMETHYLAMINOPROPYLAMINE (DMAPA)

(75) Inventors: Gregory J. Ward, Gulf Breeze, FL (US); Bryan C. Blanchard, Milton, FL (US)

(73) Assignee: Solutia Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/731,733

(22) Filed: Dec. 9, 2003

(65) Prior Publication Data

US 2004/0147784 A1 Jul. 29, 2004

Related U.S. Application Data

(63) Continuation-in-part of application No. 10/327,765, filed on Dec. 23, 2002, now Pat. No. 6,660,887.

(51) Int. Cl.$^7$ ............................................. C07C 209/48
(52) U.S. Cl. ....................... 564/490; 564/493
(58) Field of Search ................. 564/490, 493

(56) References Cited

U.S. PATENT DOCUMENTS

| | | | |
|---|---|---|---|
| 3,821,305 A | 6/1974 | Bartalini et al. ......... | 260/563 K |
| 4,289,908 A | 9/1981 | Becker et al. ............... | 564/490 |
| 4,429,159 A | 1/1984 | Cutchens et al. ........... | 564/492 |
| 4,532,354 A | 7/1985 | Cornils et al. .............. | 564/498 |
| 4,739,120 A | 4/1988 | Zuckerman ................. | 564/385 |
| 4,885,391 A | 12/1989 | Herkes ........................ | 564/491 |
| 4,967,006 A | 10/1990 | Carr ............................ | 564/490 |
| 5,097,073 A | 3/1992 | Abe et al. ................... | 564/493 |
| 5,101,075 A | 3/1992 | Käsbauer et al. ........... | 564/490 |
| 5,130,491 A | 7/1992 | Zimmerman ................ | 564/490 |
| 5,571,943 A | 11/1996 | Borninkhof et al. ........ | 564/493 |
| 5,789,621 A | 8/1998 | Schnurr et al. ............. | 564/490 |
| 5,840,989 A | 11/1998 | Cordier et al. .............. | 564/490 |
| 5,869,653 A | 2/1999 | Johnson ...................... | 540/531 |
| 5,874,625 A | 2/1999 | Elsasser ...................... | 564/490 |
| 5,894,074 A | 4/1999 | Fuchs et al. ................ | 564/490 |
| 5,898,085 A * | 4/1999 | Herkes et al. .............. | 564/490 |
| 6,248,925 B1 | 6/2001 | Ford et al. .................. | 564/470 |
| 6,281,388 B1 | 8/2001 | Goodwin, III et al. ..... | 564/492 |
| 6,469,211 B2 | 10/2002 | Ansmann et al. ........... | 564/415 |
| 2002/0058841 A1 | 5/2002 | Ansmann et al. ........... | 564/415 |

FOREIGN PATENT DOCUMENTS

| | | | |
|---|---|---|---|
| EP | 0 316 761 | 11/1988 | ........... C07C/85/12 |

OTHER PUBLICATIONS

Johnson, T.A.; Freyberger, D.P., "Lithium Hydroxide Modified Sponge Catalysts fo Control of Primary Amine Selectivity in Nitril Hydrogenations," in Catalysis of Organic Reactions, vol. 82, pp. 210–227; Ford, M.E., Marcel–Dekker; New York: 2001.*

Coq, B.; Tichit, D.; Ribet, S., "Co/Ni/Mg/Al Layered Double Hydroxides as Precursors of Catalysis for the Hydrogenation of Nitriles: Hydrogenation of Acetonitrile", *Journal of Catalysis* 2000, vol. 189; 117–128.

Huang, Y.; Sachtler, W.M.H., "Intermolecular Hydrogen Transfer in Nitrile Hydrogenation over Transition Metal Catalysts", *Journal of Catalysis* 2000, vol. 190; 69–74.

Krupka, J.; Pašek, J.; Navrátilová, M., "Hydrogenation of 3–(Dimethylamino)propionitrile over Palladiem Catalysts", *Collect. Czech. Chem. Commun.* 2000, vol. 65; 1805–1819.

Tanaka, K.; Nagasawa, M.; Sakamura, H., "Practical Synthesis of (6–Chloro–3–pyridyl)methylamine by Highly Selective Hydrogenation of 6–Chloro–3–pyridinecarbonitrile with Improved Raney Nickel Catalyst", *Bull. Chem. Soc. Jpn.* 2000, vol. 73; 1227–1231.

* cited by examiner

*Primary Examiner*—Brian Davis
(74) *Attorney, Agent, or Firm*—Howrey LLP; John Foryt

(57) ABSTRACT

An improved process for the production of 3-dimethylaminopropylamine in high purity from N,N-dimethylaminopropionitrile utilizing a low pressure hydrogenation process is described. The basic process comprises contacting the nitrile with hydrogen at low pressure in the presence of a catalyst under conditions sufficient to effect the conversion of the nitrile to the primary amine product.

12 Claims, No Drawings

LOW PRESSURE PROCESS FOR MANUFACTURE OF 3-DIMETHYLAMINOPROPYLAMINE (DMAPA)

This application is a continuation-in-part of and claims priority from application Ser. No. 10/327,765, filed Dec. 23, 2002 now U.S. Pat. No. 6,660,887.

FIELD OF THE INVENTION

This invention is generally related to the manufacture of dimethylaminopropylamine (DMAPA) from dimethylaminopropionitrile (DMAPN) using a hydrogenation process. More specifically, the invention is related to the use of a low-pressure diamine hydrogenation process for the preparation of dimethylaminopropylamine from dimethylaminopropionitrile with exceptionally high selectivity using a sponge (Raney®) type catalyst with an alkali metal hydroxide solution. In particular, low-pressure hydrogenation of DMAPN to DMAPA using a sponge nickel catalyst and a 50%/50% by weight mixture of sodium hydroxide and potassium hydroxide at low temperature is disclosed.

BACKGROUND OF THE INVENTION

N,N-dimethylaminopropylamine (DMAPA, N,N-dimethyl-1,3-diaminopropane, 3-dimethylaminopropylamine) is an important intermediate in the large-scale production of a variety of industrial processes. For example, DMAPA is an important intermediate as a surfactant for the production of soft soaps and other products, as an intermediate for the production of betaines and fatty amine oxides. N,N-dimethylaminopropylamine is also used as a starting product in the production of flocculating agents (by conversion to methacrylamide), road marking paints, and polyurethanes. DMAPA has also been shown to inhibit corrosion in boiler water treatment, and is an intermediate for gasoline and motor oil additives. Owing to DMAPA's wide utility, and the fact that the products it is associated with are produced at the multi-million pound per year level, there is the constant challenge to produce the N,N-dimethylaminopropylamine in high yield and selectivity, due to the high costs associated with byproduct contamination.

One of the more common methods used for the commercial production of aliphatic amines such as dimethylaminopropylamine has been the catalytic hydrogenation of aliphatic nitriles using either batch or trickle-bed hydrogenation techniques with the use of ammonia to inhibit secondary amine formation. However, significant amounts of ammonia are needed to carry out the reaction, and industrial handling of ammonia is expensive and is associated with environmental problems. Over the years, several approaches attempted to identify optimum technology for the production of DMAPA.

U.S. Pat. No. 3,821,305 describes a hydrogenation process in the liquid phase at pressures of 20–50 atmospheres and temperatures between 60° and 100° C. in the presence of a finely divided Raney® catalyst and a caustic alkali base. As specifically described therein, hydrogen and the nitrile are fed into a liquid medium consisting of HMDA, water, caustic alkali base, and a catalyst, wherein the content of the base is in the range of 2–130 moles per mole of caustic alkali.

In U.S. Pat. No. 4,739,120, Zuckerman describes a process for the catalytic hydrogenation of an organic nitrile group to a primary amine using a rhodium catalyst and an inorganic or organic base having a pH of 8 or greater. The reaction is described as being run in a two-phase solvent system comprising an immiscible organic solvent and water.

U.S. Pat. No. 4,885,391 describes a process for the hydrogenation of $C_4$ to $C_{12}$ nitrites using a Raney® cobalt catalyst promoted with chromium in which the catalyst activity is maintained by the addition of water. The process is carried out at a temperature of about 80° to 150° C., and at a pressure of about 400 to 2500 psig, without the use of any caustic bases.

U.S. Pat. No. 4,967,006 describes the use of ammonia in alcohol instead of caustic base in order to have lower reaction pressures. However, the use of alcohol can be problematic, as it can sometimes be difficult to remove and recycle depending upon the alcohol used, and it can result in the formation of undesirable byproducts in the reaction.

Borninkhof et al. describe a process for preparing primary amines by hydrogenation of mono and/or dinitriles in U.S. Pat. No. 5,571,943. As discussed therein, nitrites are hydrogenated in the presence of a nickel and/or cobalt catalyst system on a support, optionally in combination with a solid, reaction medium-insoluble co-catalyst, wherein the catalyst (and the co-catalyst) are non-acids.

U.S. Pat. No. 5,789,621 to Schnurr, et al. describes a process for preparing amine-containing compounds by hydrogenation of nitrites using a cobalt and/or iron-containing catalyst at an elevated (150° to 400° C.) temperature and in a hydrogenation pressure range of 0.1 to 30 MPa. The process is further described as being carried out in the presence or absence of a solvent, and either batchwise or continuously in a fixed-bed reactor using either a downflow or upflow process.

In U.S. Pat. No. 5,840,989, Cordier et al. describe the use of a specially doped Raney® nickel catalyst and a process of hydrogenating nitrites to amines using this doped catalyst. A further embodiment of the process, as described therein, is the use of a partially aqueous liquid reaction medium, with the remainder of the reaction medium being a solvent such as an alcohol or an amide.

U.S. Pat. No. 5,869,653 to Johnson describes a continuous process for hydrogenating nitrites over Raney® cobalt catalysts in the absence of ammonia, and in the presence of catalytic amounts of lithium hydroxide and water. The reduction of nitrites to amines is carried out under a hydrogen pressure of 1 to 300 bars, and at temperatures of 60° to 160° C. According to the description, the catalyst is either pre-treated with lithium hydroxide in order to achieve the desired catalytic effect, or the reaction is carried out with the lithium hydroxide present in the reaction medium itself.

In U.S. Pat. No. 5,874,625, Elsasser describes an industrial batch process for the hydrogenation of organic nitrites to primary amines, using an aqueous alkali metal hydroxide, at least one Raney® catalyst, water, and hydrogen at temperatures between 150° and 220° C. and at hydrogen pressures between 250 and 2500 psi. According to the disclosure, the improvement to the process comprises eliminating the steps of drying the charge and adding water, and reducing the required water in the system to about 0.2%.

European Patent No. EP 0316,761 to Kiel and Bauer teaches that DMAPA can be made essentially free of the 1,3-propanediamine (PDA) by-product by using a sponge cobalt or nickel catalyst and a small amount of either calcium or magnesium oxide and ammonia in order to control the selectivity of the reaction in favor of the desired primary amine. This patent also suggests that the process can be carried out at temperatures between 160° C. and 180° C. at 2200 psig with batch processing.

U.S. Pat. No. 6,281,388 to Goodwin, et al. describes a method for the production of amines from nitrites using hydrogenation. The method includes the steps of feeding both hydrogen and a nitrile into a reactor containing a catalyst, water, and an inorganic base, and mixing the reaction medium to provide a uniform bulk concentration of nitrile in at least one direction across the reactor in order to minimize reactor volume. The described process can be carried out at pressures of 20–50 atmospheres and 60–120° C., using a Raney® nickel catalyst and an inorganic base.

In U.S. Pat. No. 6,469,211, Ansmann et al. describe a process for the continuous hydrogenation of nitrites and nitrites to primary amines over an activated Raney® catalyst based on an alloy of aluminum and at least one transition metal. This hydrogenation process is reportedly carried out in the absence of ammonia and basic alkali metal compounds or alkaline earth metal compounds.

US Patent Application Publication No. 2002/0058841 to Ansmann, et al. describes the activation and use of a special macroporous, shaped Raney® catalyst based on an alpha-$Al_2O_3$ alloy of aluminum and at least one transition metal for use in the hydrogenation of nitrites to primary amines. As detailed therein, the nitrile hydrogenation is carried out in an organic solvent such as DMF or NMP at a pressure of 10 to 300 bar.

The journal literature has also described approaches to the synthesis of DMAPA using hydrogenation techniques. For example, Krupka et al. in *Coll. Czech. Chem. Commun.* 2000, Vol. 65 (11), 1805–1819 describe studies of the hydrogenation of 3-(dimethylamino)propionitrile over palladium catalysts. Effects of reaction conditions, types of catalyst, and the addition of ammonia or an amine into the charge on the hydrogenation selectivity are reported. According to the results, these studies indicated that the preferred catalyst is a $Pd/SiO_2$—$Al_2O_3$ catalyst, and the formation of secondary and tertiary amines is preferred in the hydrogenation of 3-(dimethylamino)propionitrile over palladium.

Johnson, et al. in Catalysis of Organic Reactions, Vol. 82 (2000), describes the use of lithium hydroxide modified sponge catalysts for control of the primary amine selectivity in batch nitrile hydrogenations. The LiOH modified sponge cobalt catalyst used gave high primary amine selectivity control in the conversion of nitrites to primary amines, but high (750 psig) pressures were needed to effect the reaction.

However, even with the array of methods available for the synthesis of DMAPA, most are not suitable for use in the commercial manufacture of this compound. Many of the uses of DMAPA require that the compound be of high purity and free of a number of by-products. The methodologies described above, while generating the compound in synthetically acceptable yields, fail to meet the stringent requirement of the industry, e.g. producing a product in high yields that is >99% free of by-products.

Given the increased demand for highly pure DMAPA with minimal (<300 ppm) by-product contamination, there exists a need for a method of manufacturing N,N-dimethylaminopropylamine efficiently and in high selectivity (generally free of side products), in high production rates, in high yields, and with a purity greater than 99%.

SUMMARY OF THE INVENTION

The present invention is directed to an improved process for the low-pressure hydrogenation manufacture of dimethylaminopropylamine from 3-(dimethylamino)propionitrile with a selectivity greater than 99.50%. In a preferred embodiment, the basic process comprises contacting the nitrile with hydrogen in the presence of a sponge nickel catalyst under conditions suitable to effect conversion of the nitrile group to a primary amine. The improvement in the hydrogenation process resides in effecting the hydrogenation in the presence of a sponge nickel catalyst incorporating inexpensive caustic hydroxide at low pressures (45–500 psig) and temperatures (70–100° C.). To achieve a catalytic amount of caustic hydroxide in the sponge nickel, the reaction can be carried out with the caustic hydroxide dissolved in water and dispersed in the reaction medium.

DETAILED DESCRIPTION OF THE INVENTION

The use of alkaline substances in the presence of catalysts in order to enhance the selectivity of primary amine formation during the hydrogenation of nitrites has long been known. Depending on the catalyst and the conditions, nitrites can be transformed into primary, secondary or tertiary amines, and most often a mixture of amine products is formed. For commercial reasons, only one of these products is the desired product, and typically only the primary amine is the amine of interest.

Early studies in this area showed that adding ammonia to the hydrogenation mixture of a nitrile would strongly inhibit the formation of secondary amines, and other by-products. In the course of such studies, paths indicating the process for the hydrogenation of nitrites to amines has been proposed, showing both products and by-products. For example, it is known that a surface bound primary imine (1° imine) species is formed during the hydrogenation of the nitrile DMAPN. This species can be attacked by a primary amine (1° amine) such as DMAPA, and then expels ammonia in a reversible step during the formation of the secondary imine (2° imine). Hydrogenation of the 2° imine generates a 2° amine, 3,3'-iminobis(N,N'-dimethylpropylamine (di-(3-dimethylaminopropyl)amine). The formation of the 2° amine is for all practical purposes identical to the reductive amination of an aldehyde. Also worth noting is that the presence of trace amounts of impurities from the starting nitrile DMAPN, such as dimethylamine (DMA) and acrylonitrile (AN), derived from the reverse Michael addition of DMAPN to DMA and ACN, can generate problematic and difficult to remove byproducts such as N,N,N',N'-tetramethyl-1,3-propanediamine (TMPDA). A variety of other byproducts are also possible, such as n-propylamine, resulting from excess water in the reaction medium.

Of all of the byproducts which can potentially form in the catalytic hydrogenation of DMAPN to DMAPA, none are more detrimental to commercial product formation than the formation of TMPDA or the 2° amine. Both of these products are difficult to remove, and TMPDA is inseparable from DMAPA by distillation techniques. These byproducts can form additional byproducts when the contaminated DMAPA is used as an intermediate, and impart undesirable properties to the target products. Most recently, a large new DMAPA market has developed which requires DMAPA as an intermediate containing less than 300 ppm TMPDA.

Since the product amine of interest, e.g. N,N-dimethylaminoproplyamine, is typically produced at the multi-billion pound per year level, Industry's challenge is to produce the product in high yield and selectivity because at these high volumes, even a few tenths of a percent represents a significant byproduct removal and disposal problem. From an economical standpoint, these byproducts can become unmanageable and costly to dispose of unless there is a commercial use for the byproducts. Consequently, it is beneficial to develop improved and optimized technology for controlling the selectivity and yield of the primary amine product during the hydrogenation of N,N-dimethylaminopropionitrile.

It has been found, as described herein, that the incorporation of a Group IA alkali metal hydroxide, or mixture thereof, in addition to a sponge nickel catalyst, allows for increased control of the selectivity while hydrogenating DMAPN to DMAPA. The process can be carried out at low hydrogenation pressures and temperatures, thereby increasing both the yield and the selectivity in favor of the desired primary amine, 3-dimethylaminopropylamine, to as high as at least 99.0% and 99.98%, respectively. The process also has the benefit of producing less than about 300 ppm of difficult to remove byproducts such as TMPDA and the 2° amine. Further improvements associated with the present invention include lower operating costs, reduced waste generation, and reduced disposal and treatment costs associated with such hydrogenation processes.

While the invention is directed to the process for the production of 3-dimethylaminopropylamine, it is applicable to any amine including aliphatic and aromatic amines and their derivatives, such as hexamethylene diamine, propyl amines, butyl amines, benzyl amines, tallow amines, ethyl amines, etc., produced from a nitrile including aliphatic and aromatic nitrites and their derivatives such as proprionitrile, butyronitriles, tallow nitrites, acetonitriles, benzyl nitrites, etc., in which finely divided catalyst is suspended in the liquid reaction medium.

Specifically, a process for production of 3-dimethylaminopropylamine in high yield and selectivity may be carried out at pressures of 45–500 psig, preferably 45–150 psig, and at temperatures of 70° to 100° C., by feeding hydrogen and nitrile into a liquid reaction medium containing, along with the amine produced, water, inorganic base and a finely divided nickel or cobalt catalyst dispersed in the liquid components of the reaction medium. The catalyst, which preferably is sponge (e.g. Raney®) nickel, with or without promoter metals such as chromium and/or iron, loses some of its activity during hydrogenation.

To maintain a given level of catalytic activity within the catalytic mass, it is necessary for the catalyst in the reaction medium to be gradually regenerated as described by Cutchens, et al. in U.S. Pat. No. 4,429,159, which is incorporated herein by reference. This regeneration is effected by discharging a quantity of reaction medium which contains catalyst into the regeneration vessel, allowing the catalyst to settle, decanting the organic upper layer back to the reaction vessel, and washing the catalyst with water to remove contaminants from the catalyst before it is recycled to the reactor. The recycled catalyst may consist of a mixture of fresh catalyst and of recycled catalyst if addition of a small amount of fresh catalyst is required to increase the catalyst activity in the reactor.

A key to the effectiveness of the low pressure diamine hydrogenation process of the present invention is the incorporation of an effective amount of an inexpensive caustic hydroxide in the sponge nickel catalyst to enhance the selectivity of the reaction. The hydroxide is preferably a hydroxide of a Group IA ("alkali metal") element of the periodic table, selected from the group consisting of lithium, sodium, potassium, rubidium, cesium, and mixtures thereof. More preferably, the caustic alkali metal hydroxide is sodium hydroxide, potassium hydroxide, cesium hydroxide, and mixtures thereof.

The catalyst suitable for use in the present invention is a Raney® type catalyst, also known as "skeletal" or "sponge-type" metal catalysts. While both nickel and cobalt sponge catalysts are acceptable for use, it is preferred to use a Raney® nickel catalyst with the present invention due to the higher cost associated with the use of cobalt sponge catalysts.

The nickel catalyst used in the low-pressure hydrogenation process of the present invention is sponge nickel, or as it is often referred to, Raney® nickel. The catalyst is commercially available from a number of sources (W.R. Grace and Co.; Degussa; Activated Metals), or it may be manufactured using any number of methods described in the literature, for instance by Mozingo in Organic Syntheses Collected Volume 3, p. 181; and Fieser and Fieser, Reagents for Organic Synthesis, Vol. 1, pp. 723–731 and references cited therein.

An alternative catalyst which may be used with the present invention is a cobalt catalyst. Such a cobalt catalyst used in the low-pressure hydrogenation process of the present invention is sponge cobalt, also known as Raney® cobalt. The catalyst is also available commercially from a number of sources, and may be obtained synthetically using routes described in the literature.

Conventional promoters may be incorporated into or included with the sponge catalyst in conventional amounts known to those of skill in the art. Examples of such promoters suitable for incorporation into the catalyst include Group VIa and Group VIII metals such as chromium, iron, molybdenum, and the like.

The N,N-dimethylaminopropionitrile (DMAPN) which is used as the starting material (feedstock) in the present invention can be obtained commercially from a variety of sources (Acros; Aldrich Chemical Co.). Alternatively, DMAPN can be obtained synthetically by any of the processes known in the art, such as from the reaction of acrylonitrile and dimethylamine. A process of this type, namely the reaction of dimethylamine with acrylonitrile in a blow column reactor, is described in German Patent Specification No. 27 09 966. Preferably, for use in the present invention, the DMAPN is obtained from a commercial supplier and is significantly free of n-propylamine and diaminopropane.

The hydrogenation of DMAPN to DMAPA according to the present invention is conducted under conditions such that only a minimal amount of water is required for use within the reactor. The liquid portion of the reaction medium comprises two phases: an aqueous solution of inorganic base, and an aqueous solution of the catalyst. The amount of water suitable for use with the reduction process is between about 0.1 wt. % and about 10 wt. % of the weight of the reaction mixture, preferably about 2 wt. % of the reaction mixture. With respect to the ratio of water to inorganic base, the preferred range ratio is 0.5 to 10 moles of water to 1 mole of caustic alkali.

The reduction of the nitrile to the amine can be carried out under hydrogen pressures from as low as about 45 psig to as high as about 500 psig. However, the hydrogenation of DMAPN to DMAPA is preferably carried out under a hydrogen pressure of from 45 to 300 psig, more preferably at a pressure from 45 to 150 psig or at a pressure from 45 to 110 psig. The reduction of the nitrile to the amine is preferably carried out at temperatures of between about 70° C. to about 100° C., more preferably at temperatures between about 80° C. to about 100° C., and still more preferably at temperatures between 85° C. and 95° C. Most preferably, the reduction of DMAPN to DMAPA is carried out at about 100 psig and about 90° C.

As described herein, the pressure is measured in psig (pounds per square inch, gauge), wherein 1 psig=0.068 atm (or 0.069 bar). Consequently, the reduction of the nitrile to the amine according to the present invention is preferably carried out under a hydrogen pressure of from about 3.0 atm to about 10.2 atm.

The process described herein for the hydrogenation of N,N-dimethylaminopropionitrile to N,N-dimethylaminopropylamine has the ability to effect the conversion of the nitrile group to the primary amine in surprisingly high selectivity and yield while minimizing or avoiding secondary amine byproduct formation over the course of the reaction. Consequently, the product amine, DMAPA, is produced with a selectivity of greater than 99.90%, and is produced in a yield of at least 99% (based on starting DMAPN). As described herein, selectivity refers to the amount of DMAPA formed from DMAPN, including the formation of byproducts that can be generated during the course of the reaction. Specifically, the process of the present invention preferably exhibits a selectivity of at least 99.60% of DMAPN to DMAPA, more preferably exhibits a selectivity of at least 99.70% of DMAPN to DMAPA, and still more preferably exhibits a selectivity of at least 99.90% of DMAPN to DMAPA. The yield of DMAPA produced according to the present invention is preferably at least 99% based on starting DMAPN, and can be about 99.1%, about 99.2%, about 99.3%, about 99.4%, about 99.5%, about 99.6%, about 99.7%, about 99.8%, and about 99.9% based on the starting nitrile. Most preferably, the process of the present invention exhibits a selectivity of at least 99.98% and in a yield of at least 99% from N,N-dimethylaminopropionitrile.

The hydrogenation can be conducted in any conventional hydrogenation equipment suitable to effect the conversion. For example, suitable equipment includes, but is not limited to, a stirred tank or loop reactor, a continuous stirred tank reactor, a continuous gas lift reactor, a fixed-bed reactor, a trickle-bed reactor, a bubble-column reactor, or a sieve-tray reactor. Preferred methods of operation include those described in U.S. Pat. No. 6,281,388, which is incorporated herein in its entirety.

The present invention is also envisioned to be applicable to other hydrogenation processes which typically use high pressures and temperatures and sponge, or Raney®-type catalysts. Specific examples of such processes which are envisioned to be applicable are those processes which utilize a mixture containing Raney® nickel catalyst and a strong caustic base. Such processes would be expected to yield improvements similar to those described herein for the low-pressure hydrogenation of DMAPN to DMAPA. For example, the low-pressure hydrogenation of adiponitrile to hexamethylenediamine would be expected to yield similarly improved results.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Preparation of Caustic

Caustic preparation begins with obtaining distilled water that has been boiled to remove dissolved carbon dioxide. Caustic solutions are prepared in about 25 wt. % in 100 gram batches by weight. The caustic (KOH, NaOH, etc.) is added to the degassed water (~60 mL) with stirring. After complete dissolution of the caustic, additional water is added to bring the weight of the solution to a total weight of 100 grams. The solution is filtered, and stored in a closed container until use in order to minimize adsorption of $CO_2$ from the air.

Example 2

Hydrogenation Procedure

A one-liter autoclave reactor equipped with double turbine blades, dispersimax-type agitator, a coil extending to the bottom to circulate the transfer fluid from a temperature controlled bath for temperature control, and a fritted, stainless steel metal sample port below the liquid level is used to react hydrogen with 3-(dimethylamino)propionitrile. Hydrogen is fed from a cylinder equipped with a pressure gauge and a regulator to add hydrogen to the reactor when the pressure drops below the set pressure. The hydrogen flows though a mass flow meter. The 3-(dimethylamino) propionitrile (Acros) is pumped to the autoclave with an Isco Model 500D syringe pump. To the autoclave is charged 37.5 grams of sponge nickel catalyst (Degussa MC502) with iron and chromium added to promote the hydrogenation reaction (the catalyst contains about 85% nickel, 10% aluminum, 2% chromium, and 2% iron). The catalyst is washed 3 times with water and 3 times with 3-dimethylaminopropylamine (Acros; contaminated with 72 ppm TMPDA by GC analysis), each wash consisting of mixed catalyst and material in a 100 L graduated cylinder, settling the catalyst, and decanting the top 50 mL of clear liquid. The catalyst, water, and 3-dimethylaminopropylamine slurry amounting to 50 mL are then charged to the autoclave. Additionally, 265 mL of 100% 3-dimethylaminopropylamine and 6 mL of 25% (wt.) caustic solution in water is charged. The caustic solution is a blend containing 50 wt. % sodium hydroxide and 50 wt. % potassium hydroxide. The agitator is turned on, and the autoclave heated to 60° C. The autoclave is then purged three times with nitrogen, and then three times with hydrogen, before being pressurized to 7.805 atm with hydrogen. The autoclave is then heated to 90° C., and the pressured checked and maintained for 5 minutes.

The feed of 3-(dimethylamino)propionitrile containing 0.04 wt. % water is then started to the autoclave at a rate of 5 mL/minute using the syringe pump. Pressure and temperature are maintained at 7.805 atm and 90° C., respectively, during the entirety of the run. After 27 minutes, the feed is stopped, and a 150 g sample is withdrawn from the autoclave for analysis. The feed is then resumed under the same conditions as before. This procedure is then repeated for a total of 7 cycles.

The reaction mixture was sampled after each cycle and analyzed for purity, reaction progress, and the presence and amount of by-products (if any) formed. Analysis was by gas chromatography (HP 5890 Series II; Phenomenex Zebron ZB-1 capillary column, Phenomenex Cat. No. 7HK-G001-36) with flame ionization detection in order to quantify the by-product impurities. Analysis of the cycles and the product are given in Table 1.

TABLE 1

Product analysis, per cycle.
Amounts of Byproducts Using External Standard Calibration, ppm

| Cycle | n-pa ppm | dap ppm | dmapn ppm | tmpda ppm | 2° amine ppm | water ppm |
|---|---|---|---|---|---|---|
| 1 | 89 | 0 | 0 | 43 | 200 | 7.26 |
| 2 | 123 | 0 | 0 | 29 | 267 | 4.72 |
| 3 | 143 | 0 | 0 | 17 | 284 | 3.47 |
| 4 | 174 | 0 | 0 | 14 | 308 | 2.65 |
| 5 | 190 | 0 | 0 | 7 | 265 | 2.11 |
| 6 | 209 | 0 | 0 | 5 | 236 | 1.71 |
| 7 | 223 | 0 | 0 | 0 | 214 | 1.37 | n-pa = n-propylamine
dap = 1,3-diaminopropane
dmapn = dimethylaminopropionitrile
tmpda = N,N,N',N'-tetramethyl-1,3-propanediamine
2° amine = 3,3'-iminobis(N,N-dimethylpropylamine)

Table 1 shows that the amount of secondary amine remains generally at or below 300 ppm over the course of the entire reaction when DMAPN was hydrogenated utilizing a sponge nickel catalyst and a Group IA alkali metal hydroxide according to the process of the present invention. The amount of TMPDA formed, stemming from impurities found in the feed DMAPA used to prepare the catalyst slurry, decreased over the course of the reaction, resulting in the final product being free of this common and difficult to remove by-product.

As is evident from the data shown in Table 1, the product 3-(dimethylamino)propylamine results in a molar yield of 99.98% with a purity of >99% and no TMPDA or other secondary amine impurity and less than 300 ppm of the secondary amine present in the final product.

Example 3

Hydrogenation of DMAPN Over Sponge Nickel with Different Alkali Metal Hydroxides Added A series of runs was carried out to determine the effect of various alkali metal hydroxide additions to a sponge nickel catalyst for the hydrogenation using the same procedures detailed in examples 1 and 2. The 50 wt. % sodium hydroxide and 50 wt. % potassium hydroxide caustic solution specified in example 2 was substituted with an aqueous solution of the alkali metal hydroxide at the level indicated in Table 2. After the reaction number of cycles indicated in Table 2, a sample was removed for gc analysis. The amount of DMAPN remaining and the amount of various secondary amine side products generated was recorded. The conditions and results are clearly shown in Table 2.

TABLE 2

Effect of Alkali Metal Hydroxide n Activity and Selectivity

| Run | Catalyst | Amt. Catalyst | Alkali Metal Hydroxide | Metal Hydroxide Amount | Temp./Press. °C./psig | Number of Cycles | DMAPN Remaining (ppm) | 2° amine (ppm) |
|---|---|---|---|---|---|---|---|---|
| 1 | Ni-MC502 | 37.5 g | NaOH | 8 mL of 25% (wt) aqueous NaOH | 90/110 | 6 | 163 | 1440 |
| 2 | Ni-MC502 | 37.5 g | KOH | 6 mL of 25% (wt) aqueous KOH | 90/100 | 6 | 0 | 9 |
| 3 | Ni-MC502 | 37.5 g | RbOH | 7 mL of 25% (wt) aqueous RbOH | 90/100 | 6 | 0 | 1463 |
| 4 | Ni-MC502 | 37.5 g | CsOH | 8 mL of 25% (wt) aqueous CsOH | 90/500 | 6 | 0 | 15 |
| 5 | Ni-MC502 | 37.5 g | LiOH | 80 mL of 10% (wt) aqueous LiOH | 90/500 | 6 | 0 | 2567 |
| 6 | Ni-MC502 | 37.5 g | KOH/NaOH | 6 mL of 25% (wt) aqueous 50/50 NaOH/KOH | 90/100 | 6 | 0 | 9 |

See Table 1 for the identification of acronyms.

Tables 1 and 2 clearly show that the use of such alkali metal hydroxides as KOH, CsOH, and mixtures of KOH/NaOH allowed the reaction to proceed to a high DMAPN conversion, e.g., a low DMAPN concentration remained in the product DMAPA within a reasonable time and also maintaining a high selectivity for the primary amine. The use of LiOH (run 5) showed a poor improvement in the amount of side-product formation using the same catalyst as in the other tests. From these results, to maintain a high rate of selectivity in the hydrogenation of dimethylaminopropionitrile to dimethylaminopropylamine, KOH, CsOH, and mixtures of KOH/NaOH are most effective as alkali metal hydroxides.

All of the methods and processes disclosed and claimed herein can be made and executed without undue experimentation in light of the present disclosure. While the methods of this invention have been described in terms of preferred embodiments, it will be apparent to those of skill in the art that variations may be applied to the methods and/or processes and in the steps or in the sequence of steps of the methods described herein without departing from the concept, spirit and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the invention.

What is claimed is:

1. A process for the production of N,N-dimethylaminopropylamine from N,N-dimethylaminopropionitrile by low pressure hydrogenation comprising:

feeding hydrogen and N,N-dimethylaminopropionitrile into a low-pressure reactor containing a sponge nickel catalyst, at least one Group IA alkali metal hydroxide, and water to form a reaction medium;

heating the reaction medium to a temperature of about 70° C. to about 100° C.;

pressurizing the reactor to a pressure of about 45 psig to about 500 psig;

mixing the reaction medium; and hydrogenating the nitrile to form N,N-dimethylaminopropylamine.

2. The process of claim 1, wherein the selectivity of N,N-dimethylaminopropionitrile to N,N-dimethylaminopropylamine is greater than about 99.60%.

3. The process of claim 1, wherein the selectivity of N,N-dimethylaminopropionitrile to N,N-dimethylaminopropylamine is greater than about 99.90%.

4. The process of claim 1, wherein the Group IA alkali metal hydroxide is selected from the group consisting of sodium hydroxide, potassium hydroxide, rubidium hydroxide, cesium hydroxide and mixtures thereof.

5. The process of claim 1 wherein the Group IA alkali metal hydroxide is potassium hydroxide.

6. The process of claim 1 wherein the Group IA alkali metal hydroxide is sodium hydroxide.

7. The process of claim 1 wherein the Group IA alkali metal hydroxide is a mixture of sodium hydroxide and potassium hydroxide.

8. The process according to claim 1 wherein the temperature is between 85° C. and 95° C.

9. The process of claim 1 wherein the pressure is between 45 psig and 300 psig.

10. The process of claim 1 wherein the pressure is between 45 psig and 150 psig.

11. The process of claim 1 wherein the pressure is between 45 psig and 110 psig.

12. The process of claim 1 wherein the amount of water is about 0.1 wt. % to about 10 wt. % of the reaction medium.

* * * * *